United States Patent [19]

Cuscurida et al.

[11] Patent Number: 4,994,627
[45] Date of Patent: Feb. 19, 1991

[54] PURIFICATION OF POLYOXYALKYLENE GLYCOLS

[75] Inventors: Michael Cuscurida, Austin; Arthur J. Faske, Cedar Park, both of Tex.

[73] Assignee: Texaco Chemical Company, White Plains, N.Y.

[21] Appl. No.: 494,353

[22] Filed: Mar. 16, 1990

[51] Int. Cl.$^5$ .............................................. C07C 41/36
[52] U.S. Cl. .................................................. 568/621
[58] Field of Search ........................................ 568/621

[56] References Cited

U.S. PATENT DOCUMENTS 4,518,396  5/1985  Rawson ............................. 568/621

FOREIGN PATENT DOCUMENTS 878460  9/1961  United Kingdom ................ 562/621

Primary Examiner—Howard T. Mars

Attorney, Agent, or Firm—Jack H. Park; Kenneth R. Priem; Carl G. Ries

[57] ABSTRACT

A feedstock selected from the group consisting of polyoxyethylene glycols, polyoxypropylene glycols and monoalkyl ethers thereof having molecular weights of about 200 to about 5,000 and contaminated with more than about 100 ppm of alkali metal or alkaline earth metal ions is purified by bringing said feedstock into contact with a basic ion exchange resin in the presence of about 2 to about 10 wt. % of water, based on the weight of the feedstock at a temperature of about 25° to about 100° C. and a pressure of about 0 to about 100 psig. for a period of time sufficient to lower the impurity level of said ions by at least about 90% to a level of less than about 100 ppm, the basic ion exchange resin being a fully hydrated boron specific basic styrene-divinyl benzene ion exchange resin in the free base form having an apparent density of about 40 to 45 lbs. per cubic foot.

14 Claims, No Drawings

PURIFICATION OF POLYOXYALKYLENE GLYCOLS

BACKGROUND OF THE INVENTION

1. Technical Field of the Invention

This invention relates to a method for the purification of a polyoxyalkylene feedstock selected from the group consisting of polyoxyethylene glycols, polyoxypropylene glycols and $C_1$–$C_4$ monoalkyl ethers thereof having molecular weights of about 200 to about 5,000 and contaminated with more than about 100 parts per million of alkali metal or alkaline earth metal ions. In accordance with the present invention, the feedstock of the present invention is mixed with about 2 to about 10 wt. % of water, based on the weight of the feedstock and, if the feedstock is a polyoxypropylene glycol or a $C_1$–$C_4$ monoalkyl ether thereof, it is additionally mixed with from about 30 to about 70 wt. % of a polar organic solvent. The resultant charge stock, comprising a feedstock contaminated with more than about 100 parts per million of alkali metal or alkaline earth metal ions is brought into contact with a basic ion exchange resin (Amberlite ® IRA-743, a styrene-divinyl benzene ion exchange resin in the free base form) under treating conditions including a temperature of about 25° to about 100° C. and a pressure of 0 to about 100 psig. for a period of time sufficient to lower the impurity level of the ions in the feedstock by at least about 90% to an impurity level of less than about 100 parts per million.

The basic ion exchange resin to be used in accordance with the present invention is a fully hydrated boron specific basic styrene-divinyl benzene ion exchange resin in the free base form having an apparent density of about 40 to 45 lbs. per cubic foot.

2. Prior Art

Amberlite ® IRA-743 is a boron specific ion exchange resin manufactured by the Rohm and Haas Company of Philadelphia, Pa. The precise composition of the ion exchange resin is the proprietary information of the Rohm and Haas Company who, in their brochures, describe the ion exchange resin as a boron-specific ion exchange resin in the free base form, that applicant understands to be a styrene-divinyl benzene ion exchange resin, that is sold as fully hydrated spherical particles having a moisture content of about 58% and an apparent density of about 40 to 45 lbs. per cubic foot (640-720 g/l). Rohm and Haas state that Amberlite ® IRA-743 is a unique ion exchange resin that is specific for borate and boric acid under a variety of conditions. This is the only stated use for the product.

The use of Amberlite ® IRA-743 is described in an article entitled: "Boron Removal from Industrial Effluent by Ion Exchange" by Buzzard et al. (*Toxic Hazard Wastes*, 1987, 218–226).

Another use of the resin for the removal of boric acid and related compounds from solutions of carbohydrates is described by Hicks et al. (*Carbohydr. Res,* 1986, 147(1), pages 39–48).

Yet another use of Amberlite ® IRA-743 in the treatment of wastewater containing fluoroborates is disclosed by Iwaya, Yoshiaki et al. in JPN. KOKAI TOKKYO JP 60,172,39 [85,172,392] (Cl. C02f/42) 05 Sept. 1983, Appl. 84/29,235, 17 Feb. 1984.

Still another use of the resin for the recovery of boron from natural gas brines is disclosed by Yasuda, Sejii et al. (Gov. Ind. Res. Inst., Tosu, Japan 841 *Nippon-Kagaku Kaishi* 1987, (4), 752-6 (Japan).

Amberlite ® IRA-743 has also been used to remove arsenic from wastewater Unitaka Ltd. Jpn. Kokai Tokkyo Kobe JP 58 64,180 [83 64,180] (Cl. C02F1/42). 16 Apr. 1983, Appl. 81/163,819.

BACKGROUND INFORMATION

Polyoxyethylene glycols, polyoxypropylene glycols, poly(oxyethylene/oxypropylene) glycols and the $C_1$–$C_4$ monoalkyl ethers thereof are conventionally prepared by the epoxidation of a hydroxy-containing initiator such as ethylene glycol, propylene glycol or a $C_1$–$C_4$ alkyl alcohol with ethylene oxide, propylene oxide or both ethylene oxide and propylene oxide. The alkoxylation reaction is promoted with a basic material such as an alkali metal or alkaline earth metal hydroxide. As a consequence, at the end of the alkoxylation step, &he desired polyoxyethylene glycol, polyoxypropylene glycol or $C_1$–$C_4$ monoalkyl ether thereof will be contaminated with a significant quantity of alkali metal or alkaline earth metal ions such as sodium ions, potassium ions, cesium ions, etc., the contamination normally being at a level above 100 parts per million based on the alkoxylation product and more typically being from about 300 to about 10,000 parts per million.

Conventionally, the alkali metal and alkaline earth metal ions are removed from the alkoxylation product by water extraction, neutralization with an acidic material or by chemical adsorption. Although the conventional purification techniques are generally satisfactory, they tend to be time-consuming and expensive and there is need for improvement.

SUMMARY OF THE INVENTION

The present invention is directed to the purification of a feedstock selected from the group consisting of polyoxyethylene glycols, polyoxypropylene glycols and $C_1$–$C_4$ monoalkyl ethers thereof which are contaminated with more than 100 parts per million, and more typically from 300 to 10,000 parts per million of alkali metal and/or alkaline earth metal ions.

It has been discovered in accordance with the present invention that if the feedstock is mixed with from about 2 to about 10 wt. % of water, based on the weight of the feedstock and then brought into contact with a basic ion exchange resin (Amberlite ® IRA-743) under treating conditions including a temperature of about 25° to about 100° C. and a pressure of about 0 to about 100 psig., the impurity level of the feedstock can be reduced by 90% or more to a level of less than about 100 parts per million of alkali metal or alkaline earth metal ions.

When the feedstock is a polyoxypropylene glycol or a $C_1$–$C_4$ monoalkyl ether thereof, the feedstock will tend to be immiscible with the added water, and therefore, it is desirable in this situation to also add from about 30 to about 70 wt. % of a polar organic solvent, based on the weight of the feedstock in order to enhance water miscibility.

DESCRIPTION OF THE PREFERRED EMBODIMENT

The starting materials for the present invention are a feedstock selected from the group of polyoxyethylene glycols, polyoxypropylene glycols, poly(oxyethylene/oxypropylene) glycols and $C_1$–$C_4$ monoalkyl ethers thereof having molecular weights within the range of about 200 to about 5,000 and contaminated with more than 100 parts per million, and more typically from about 300 to about 10,000 parts per million of alkali metal and alkaline earth metal ions. Other starting materials to be used include water and, when the feedstock is a polyoxypropylene glycol or a $C_1$–$C_4$ alkyl ether thereof, a polar organic solvent such as a $C_1$–$C_4$ alkyl alcohol (e.g., methanol, ethanol, propanol, n-butanol, isobutanol, etc.)

The basic ion exchange resin to be used in accordance with the present invention is an article of commerce sold by the Rohm and Haas Corporation under the tradename Amberlite® IRA-743. Amberlite® IRA-743 is a boron-specific ion exchange resin which is normally used to remove boron ions from a feedstock. It may be further characterized as a boron-specific styrene-divinyl benzene ion exchange resin the the free base form.

It has been surprisingly discovered in accordance with the present invention that Amberlite IRA-743 is effective not only for the removal of boron ions from a feedstock, but is also effective for the removal of alkali metal and alkaline earth metal ions from the feedstocks of the present invention provided that the feedstock is mixed with about 2 to about 10 wt. % of water before it is brought into contact with the ion exchange resin.

As indicated, the polyoxypropylene glycols and the $C_1$–$C_4$ monoalkyl ethers thereof tend to be immiscible with water and therefore it is desirable that such feedstocks be additionally mixed with from about 30 to about 70 wt. % of a polar organic solvent such as a $C_1$–$C_4$ alkyl alcohol.

The present invention is preferably conducted in a continuous fashion by passing a charge stock composed of the polyoxyalkylene feedstock of the present invention, about 2 to about 10 wt. % of water and, in the case of the polyoxypropylene glycols and $C_1$–$C_4$ monoalkyl ethers thereof, with a polar organic solvent by continuously passing the thus-prepared charge stock through a bed of a basic ion exchange resin consisting essentially of Amberlite IRA-743 under treating conditions including a space velocity of about 0.1 to about 1 volume of feedstock per hour per volume of basic ion exchange resin, a temperature of about 25° to about 100° C. and a pressure of about 0 to about 100 psig. to thereby lower the level of contamination of the feedstock with alkali metal and alkaline earth metal ions by at least about 90% to a level of less than about 100 parts per million.

The charge stock, after passage through the bed of basic ion exchange resin is resolved, preferably by suitable distillation, such as vacuum distillation, into a decontaminated feedstock containing less than 100 parts per million of alkali metal and alkaline earth metal ion contaminants and the other components of the charge stock including water and the polar organic solvent.

The charge stocks of the present invention are polyoxyalkylene glycols, polyoxyethylene glycols, polyoxypropylene glycols and $C_1$–$C_4$ alkyl ethers thereof having molecular weights of about 200 to about 5,000, and more preferably, from about 200 to about 2,000. The feedstocks of the present invention will typically be contaminated with more than about 100 parts per million of alkali metal and alkaline earth metal ions and more typically, from about 300 to about 10,000 parts per million of alkali metal and alkaline earth metal ions.

The alkali metal and alkaline earth metal contaminants are present in the feedstock because the feedstock is typically prepared by the propoxylation and/or ethoxylation of a hydroxy-containing initiator such as a glycol or a $C_1$–$C_4$ alkyl alcohol in the presence of an alkaline earth metal hydroxide or alkali metal hydroxide catalyst such as sodium hydroxide, potassium hydroxide, cesium hydroxide, etc.

The polyoxyethYlene glcyols and the $C_1$–$C_4$ monoalkyl ethers thereof are water soluble whereas the polyoxypropylene glycols and the $C_1$–$C_4$ monoalkyl ethers thereof tend to be immiscible with water, especially the higher molecular weights above about 500.

The charge stock of the present invention is prepared by mixing a polyoxyalkylene feedstock, as above described, with about 2 to about 10 wt. % of water. In order to ensure water miscibility, when the feedstock is a polyoxypropylene glycol or a $C_1$–$C_4$ monoalkyl ether therof, the feedstock is additionally mixed with from about 30 to about 70 wt. % of a polar organic solvent such as methanol, ethanol, propanol, isopropanol, butanol, tertiary butyl alcohol, etc.

Surprisingly, when a charge stock, as above defined, is brought into contact with the basic ion exchange resin (Amberlite® IRA-743), as defined herein, under treating conditions including a space velocity of about 0.1 to about 1 volume of feedstock per hour per volume of basic ion exchange resin, a temperature of about 25° to about 100° C. and a pressure of 0 to 100 psig., the level of alkali metal and/or alkaline earth metal contamination in the feedstock is reduced by 90 wt. % or more to a level of about 100 parts per million or less.

SPECIFIC EXAMPLES

The invention will be further illustrated by the following specific examples which are given by way of illustration and not as limitations on the scope of the present invention.

EXAMPLE 1

This example will illustrate the use of the Amberlite IRA-743 basic ion-exchange to remove cesium from a sample of a 2000 m.w. polyoxypropylene glycol which contained 5300 ppm cesium.

200 grams of the 2000 m.w. polyoxypropylene glycol, which contained 5300 ppm cesium, was first dissolved in 100 g t-butanol. Six grams water were then mixed into the polyol/t-butanol solution and the mixture heated to 80° C. The polyol/t-butanol/water mixture was then allowed to pass through a 50×2.1 cm column which had been packed with 150 ml of the Amberlite® IRA-743 basic ion-exchange resin. The effluent was then vacuum stripped at 100° C. and 5 mn Hg to remove the t-butanol and water. Results are shown in the following table:

| Sample No. | 6445-71A | 6445-71B* |
|---|---|---|
| Flow rate, ml/hr | 50-60 | — |
| Results | | |
| Cesium, ppm | 2.3 | 5300 |
| pH in 10:6 isopropanol-water | 7.05 | — |

*Starting Material

EXAMPLE 2

This example will show the use of the Amberlite IRA-743 basic ion-exchange resin to remove potassium from an alkaline sample of the six mole ethylene oxide adduct of methanol which contained 330 ppm potassium.

Water (12.5 g) was added to 250 g of the alkaline six mole ethylene oxide adduct of methanol and passed through the ion-exchange column described in Example 1. The column had been regenerated using 10% sulfuric acid and 4% ammonium hydroxide followed by a water wash. Results are as follows:

| Sample No. | 6445-74A | 6445-74B* |
|---|---|---|
| Flow rate, ml/hr | 120 | — |
| Column temperature, °C. | 25 | — |
| Results | | |
| Potassium, ppm | 32 | 330 |
| Sodium, ppm | 1.0 | 1.4 |
| pH in 10:6 isopropanol-water | 7.8 | — |

*Starting Material

EXAMPLE 3

This example will demonstrate the use of Amberlite IRA-743 basic ion-exchange resin to remove calcium from a 2000 m.w. polyoxypropylene glycol which contained 830 ppm dissolved calcium.

200 grams of the calcium-containing TEXOX® PPG-1000, 100 g t-butanol, and 12.5 g of water were passed through the ion-exchange column described in Example 1 and regenerated as described in Example 2. Results are as follows:

| Sample No. | 6445-71A | 6445-71B |
|---|---|---|
| Flow rate, ml/hr | Standard | 40–50 |
| Temperature, °C. | — | 50 |
| Results | | |
| Calcium, ppm | 830 | 20 |

Having thus described our invention, what is claimed is:

1. A method for the purification of a polyoxyalkylene feedstock selected from the group consisting of polyoxyethylene glycols, polyoxypropylene glycols and $C_1$–$C_4$ monoalkyl ethers thereof having molecular weights of about 200 to about 5,000 and contaminated with more than about 100 ppm of alkali metal or alkaline earth metal ions which comprises contacting said feedstock with a basic ion exchange resin in the presence of from about 2 to about 10 wt. % of water, based on the weight of the feedstock, at a temperature of about 25° to about 100° C. and a pressure of about 0 to about 100 psig. for a period of time sufficient to lower the impurity level of said ions in said feedstock by at least about 90% to an impurity level of less than about 100 ppm,
said basic ion exchange resin being a fully hydrated boron specific basic styrene-divinyl benzene ion exchange resin in the free base form having an apparent density of about 40 to 45 lbs. per cubic foot.

2. A method as in claim 1 wherein the process is conducted on a continuous basis by continuously passing said feedstock through a bed of said basic ion exchange resin at a space velocity of about 0.1 to 1 volumes of said feedstock per hour per volume of said basic ion exchange resin.

3. A method as in claim 2 wherein the feedstock is a polyoxyethylene glycol.

4. A method as in claim 2 wherein the feedstock is a $C_1$–$C_4$ monoalkyl ether of a polyoxyethylene glycol.

5. A method as in claim 2 wherein the feedstock is a polyoxypropylene glycol and wherein the feedstock is additionally mixed with about 30 to about 70 wt. %, based on the weight of the feedstock of a polar organic solvent.

6. A method as in claim 5 wherein the polar organic solvent is a lower aliphatic alcohol containing 1 to 4 carbon atoms.

7. A method as in claim 6 wherein the lower aliphatic alcohol is t-butanol.

8. A method as in claim 2 wherein the feedstock is a $C_1$–$C_4$ monoalkyl ether of a polyoxypropylene glycol and wherein the feedstock is additionally mixed with about 30 to about 70 wt. %, based on the weight of the feedstock, of a polar organic solvent.

9. A method as in claim 8 wherein the polar organic solvent is a lower aliphatic alcohol containing 1 to 4 carbon atoms.

10. A method as in claim 9 wherein the lower aliphatic alcohol is t-butanol.

11. A method for substantially decontaminating a feedstock selected from the group consisting of polyoxyethylene glycols, polyoxypropylene glycols and $C_1$–$C_4$ monoalkyl ethers thereof having molecular weights of about 200 to about 5,000 and initially contaminated with at least about 300 ppm of alkali metal or alkaline earth metal ions, said method comprising the steps of:
adding about 30–70 wt. % of a polar organic solvent when the feedstock is a polyoxypropylene glycol or a $C_1$–$C_4$ monoalkyl ether thereof to establish water miscibility,
adding to the feedstock from about 2 to about 10 wt. % of water, based on the weight of the feedstock, to prepare a charge stock,
passing said charge stock through a bed of a basic ion exchange resin under treating conditions including a flow rate of about 0.1 to 1 volumes of said charge stock per hour per volume of said ion exchange resin, a temperature of about 25° to about 100° C. and a pressure of about 0 to about 100 psig., to thereby lower the impurity level of said ions in said charge stock by at least about 90% to a value of less than about 100 ppm, and
distilling said charge stock to separate said feedstock from the other components of said charge stock,
said basic ion exchange resin being a fully hydrated boron specific basic styrene-divinyl benzene ion exchange resin in the free base form having an apparent density of about 40 to 45 lbs. per cubic foot.

12. A method as in claim 11 wherein the contaminant is cesium.

13. A method as in claim 11 wherein the contaminant is potassium.

14. A method as in claim 11 wherein the contaminant is calcium.

* * * * *